US00PP09209P

United States Patent [19]

Mayer

[11] Patent Number: Plant 9,209

[45] Date of Patent: Jul. 18, 1995

[54] 'BA 73-381' KENTUCKY BLUEGRASS

[75] Inventor: Virgil D. Meier, Marysville, Ohio; J. Kevin Turner, South Salem, Oregon; Eugene W. Mayer, Marysville, Ohio

[73] Assignee: OMS Investments, Inc., Wilmington, Del.

[21] Appl. No.: 308,699

[22] Filed: Sep. 19, 1994

[51] Int. Cl.[6] ..... A01H 5/00

[52] U.S. Cl. ..... Plt./90.2

[58] Field of Search ..... Plt. 90.2

*Primary Examiner*—James R. Feyrer

*Attorney, Agent, or Firm*—Jones, Day, Reavis & Pogue

[57] ABSTRACT

A variety of Kentucky bluegrass having a medium to high level of resistance to leaf spot, melting out disease, rust diseases, and stripe smut; a desirable green color throughout the growing season; the ability to form a turf of good quality under a wide variety of environmental conditions; a moderately wide blade and a high level of seed yielding capacity.

1 Drawing Sheet

BACKGROUND OF THE INVENTION

1. Field of the Invention

The present invention relates to a new and distinct variety of Poa pratensis that has been designated Ba 73-381 Kentucky bluegrass.

2. Description of Related Art

Kentucky bluegrasses have been disclosed in U.S. Plant Pat. Nos. 3,156, issued May 9, 1972; 3,186, issued May 23, 1972; 4,336, issued Nov. 28, 1978; 6,280, issued Sep. 6, 1988; 6,537 and 6,538, issued Jan. 17, 1989; 6,585, issued Feb. 7, 1989, 7,831, issued Mar. 17, 1992; 8,490, issued Dec. 7, 1993 and pending U.S. Plant patent application Ser. No. 08/125,564, filed Sep. 23, 1993.

SUMMARY OF THE VARIETY

Ba 73-381 Kentucky bluegrass plant material originated by crossing an unreleased Kentucky bluegrass selection (Bd65-26-1) from the O. M. Scott and Sons breeding program with a Merion Kentucky bluegrass plant as the pollen parent. As a result of this breeding, a distinct variety was produced and asexually propagated by rhizomes, tillers and disseminules.

Seed of Ba 73-381 was produced first at Marysville, Ohio and later at Gervais, Oreg. This seed was used to plant turf performance evaluation trails and later seed production fields. Asexual production of Ba 73-b 381 by propagules (tillers and rhizomes) and by disseminules (modified caryopses produced by apomixis) has consistently produced progeny plants indistinguishable from the mother plant. The apomixis level of Ba 73-381 is approximately 99% based upon examining seedling characteristics of approximately 100 to 150 seedlings from six different crop years in a growth chamber.

Ba 73-381 has a number of highly desirable characteristics including a medium to high level of resistance to Drechslera spp. formerly called Helminthosporium spp. that causes leaf spot, melting out and crown rot, Puccinia spp. that causes several tupes of rust infections, and *Ustilago striiformis* that causes strip smut. Ba 73-381 has an attractive leafy turf type growth habit, moderately wide leaf blades, attractive green color which can be maintained throughout the entire growing season, and good turf performance as evidenced by consistently good scores for quality and color. Ba 73-381 has a high seed yield potential in the bluegrass seed production region of northwestrn U.S.A.

In comparison with a number of other Kentucky bluegrasses, Ba 73-381 differs significantly in regard to the following morphological characteristics: (1) seed width, (2) floret number, (3) flag leaf ligule hair, (4) vegetative leaf margin hair, (5) peduncle width and (6) vegetative leaf ligule length.

Ba 73381 has a large seed, below average seed count and a long rachilla, a short and narrow panicle, a high whorl and branch count, average size spikelets, a low floret count and average size glumes. Ba 73-381 has a medium length culm, a low node count, an average internode length, a medium length but above averge peduncle width. The flag leaf is average in length and width but above average in thickness, has a long ligule and a statistically higher ligule hair content than most other bluegrasses in the evaluation. The vegetative leaf of Ba 73-381 is long, slightly below average in width but average in thickness, a short ligule and a low population of leaf margin hairs. The vegetative leaf under close mowing practiced under lawn maintenance conditions has a statistically broader leaf than a number of other Kentucky bluegrasses.

DETAILED DESCRIPTION OF THE VARIETY

Figure 3:
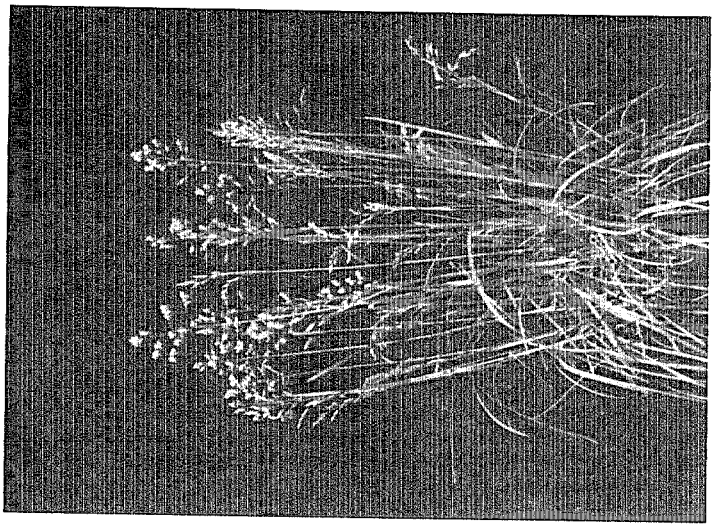
FIG. 3 is a ba 73-381 Kentucky bluegrass plant during anthesis.
Figure 2:
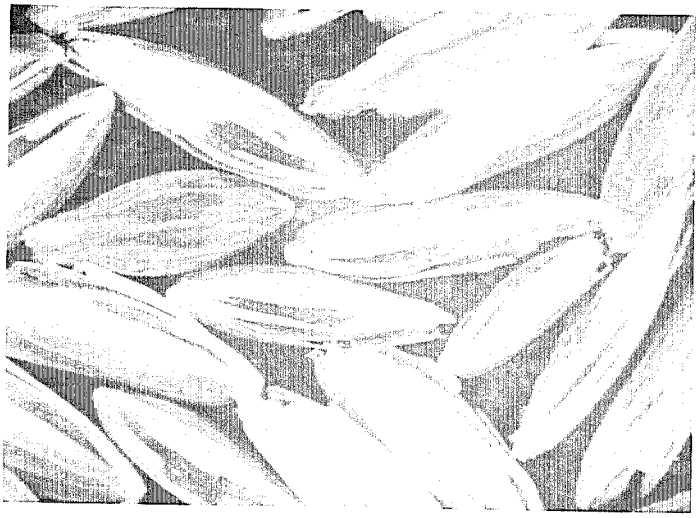
FIG. 2 is Ba 73-381 Kentucky bluegrass seed.
Figure 1:
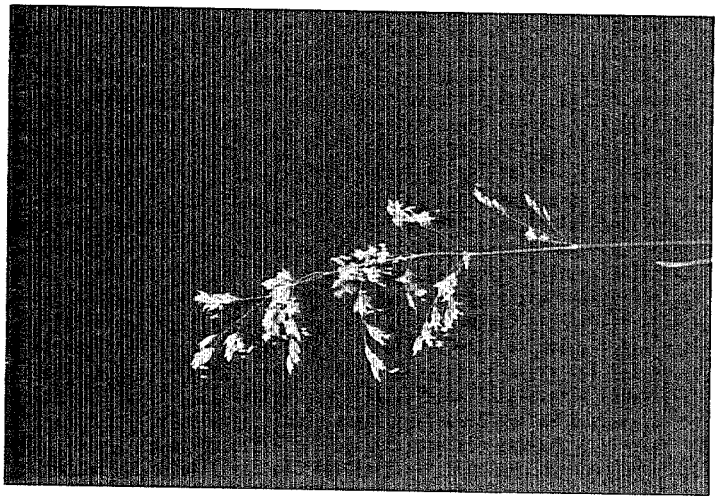
FIG. 1. is a Ba 73-381 Kentucky bluegrass panicle.

Ba 73-381 Kentucky bluegrass (*Poa pratensis* L.) is a perennial with creeping rhizomes forming a dense turf. When plants overwinter in the filed under freezing temperatures and are then brought into the greenhouse during late winter to continue growth undisturbed by clipping under moderate temperatures (60°–80° F.), culms are erect averaging 39.5 mm in length, 3.1 nodes per culm, an uppermost internode length of 10.8 cm and a peduncle averaging 24.3 cm in length, and 0.808 mm in width. The vegetative leaf averages 22.1 cm in length, 3.3 mm in width, 0.300 mm in thickness, 0.16 mm in ligule length and a low leaf margin hair count. The flag leaf averages 4.3 cm in length, 3.5 mm in width, 0.223 mm in thickness, a ligule length of 1.3 mm and a high ligule hair count. The panicle averages 80.2 mm in length, 55.3 mm in width and 9.8 whorls. The lowest whorl averages 4.1 branches and the third whorl from the bottom of the panicle 3.9 branches (Table 3). The spikelets in the lowest whorl average 4.7 mm in length, 2.4 mm in width and 2.7 florets. The outer glume from the lowerst whorl averages 2.8 mm in length and the inner glume 3.2 mm in length. The spikelet from the third whorl averages 4.6 mm in length, 2.6 mm in width, and 2.7 florets.

The outer glume from the third whorl averages 2.9 mm in length and the inner glume 3.1 mm in length. Conditioned seed of Ba 73-381 averages 3.00 mm in length, 0.94 mm in width, a rachilla length of 0.86 mm and approximately 1,171,000 seeds per pound. The dorsal side of the lemma keel contained an average population of hairs.

Comparisons of Ba 73-381 with other varieties in terms of seed dimensions and seed numbers per pound are shown in Tables 1 and 2 as follows:

TABLE 1

Seed and Rachilla Measurements and Lemma Hair of Ba 73-381 and Other Kentucky Bluegrass Varieties After Conditioning

| Variety | Length (mm) | Width (mm) | Rachilla (mm) | Lemma* Hair |
|---|---|---|---|---|
| Ba 73-381 | 3.00 | 0.94 | 0.86 | 4.9 |
| Ba 73-366 | 3.04 | 0.91 | 0.80 | 4.4 |
| Abbey | 2.97 | 0.89 | 0.80 | 3.8 |
| Adelphi | 2.70 | 0.84 | 0.65 | 4.4 |
| America | 2.40 | 0.68 | 0.68 | 2.8 |
| Baron | 3.08 | 0.81 | 0.71 | 5.0 |
| Bristol | 2.94 | 0.88 | 0.73 | 4.3 |
| Chateau | 2.81 | 0.86 | 0.71 | 4.5 |
| Coventry | 2.71 | 0.81 | 0.70 | 4.0 |
| Eclipse | 2.77 | 0.83 | 0.68 | 3.5 |
| Georgetown | 2.94 | 0.82 | 0.74 | 4.9 |
| Gnome | 2.78 | 0.83 | 0.75 | 4.1 |
| Kelly | 3.07 | 0.89 | 0.75 | 4.2 |
| Marquis | 2.97 | 0.87 | 0.83 | 4.7 |
| Midnight | 2.94 | 0.76 | 0.78 | 5.7 |
| Nassau | 3.07 | 0.86 | 0.68 | 3.4 |
| Ram I | 3.23 | 0.89 | 0.80 | 6.0 |
| Touchdown | 2.93 | 0.88 | 0.71 | 4.6 |
| Victa | 3.00 | 0.80 | 0.82 | 3.5 |
| LSD (.05) | 0.16 | 0.05 | 0.13 | 0.86 |

*Rating Scale 0–9: 9 = abundant row of hairs along keel.

TABLE 2

Comparison of Seed Numbers Per Pound of Ba 73-381 and Other Kentucky Bluegrass Varieties After Conditioning

| Variety | Seeds per Pound |
|---|---|
| Ba 73-381 | 1,171,000 |
| Ba 73-366 | 1,025,586 |
| Abbey | 1,003,037 |
| Adelphi | 1,383,976 |
| America | 1,659,824 |
| Baron | 1,051,693 |
| Bristol | 1,270,821 |
| Chateau | 1,300,105 |
| Coventry | 1,246,200 |
| Eclipse | 1,335,668 |
| Georgetown | 1,431,000 |
| Gnome | 1,017,641 |
| Kelly | 921,166 |
| Marquis | 1,054,642 |
| Midnight | 1,227,000 |
| Nassua | 1,127,130 |
| Ram 1 | 1,214,000 |
| Touchdown | 1,211,000 |
| Victa | 1,038,298 |

Since environmental conditions such as soil and climate may influence morphological characters to some extent, comparisons of morphological characteristics of Ba 73-381 are made with other Kentucky bluegrass varieties are given in Tables 3–8.

TABLE 3

Morphological Comparison of Panicles of Ba 73-381 and Other Kentucky Bluegrass Varieties in the Greenhouse at Marysville, OH

| | Panicle | | | Number | Number of Branches | |
|---|---|---|---|---|---|---|
| Variety | Nodding* | Length (mm) | Width (mm) | Whorls/ Panicle | Lower Whorl | Third Whorl |
| Ba 73-381 | 1.1 | 80.2 | 55.3 | 9.8 | 4.1 | 3.9 |
| Ba 73-366 | 1.6 | 88.8 | 68.4 | 8.8 | 4.3 | 3.7 |
| Abbey | 1.6 | 80.4 | 59.3 | 9.3 | 3.8 | 3.3 |
| Adelphi | 1.8 | 106.8 | 76.4 | 10.0 | 3.6 | 3.0 |
| America | 2.3 | 67.7 | 51.1 | 8.8 | 3.3 | 3.5 |
| Baron | 2.2 | 92.6 | 71.0 | 10.0 | 3.4 | 2.8 |
| Bristol | 2.0 | 85.5 | 61.5 | 8.4 | 2.8 | 2.7 |
| Chateau | 2.9 | 65.2 | 57.3 | 8.5 | 3.3 | 2.8 |
| Coventry | 2.5 | 64.0 | 54.2 | 8.4 | 3.3 | 2.5 |
| Eclipse | 1.3 | 89.2 | 74.0 | 10.7 | 3.3 | 2.1 |
| George-town | 1.0 | 80.0 | 57.0 | 7.4 | 2.1 | 2.6 |
| Gnome | 1.1 | 80.6 | 56.0 | 10.6 | 4.6 | 3.9 |
| Kelly | 2.0 | 88.0 | 70.2 | 9.8 | 4.6 | 3.7 |
| Marquis | 1.1 | 82.0 | 63.0 | 10.3 | 3.9 | 3.6 |
| Midnight | 2.0 | 75.8 | 48.4 | 7.1 | 2.9 | 3.0 |
| Nassau | 2.2 | 91.2 | 68.6 | 10.0 | 2.5 | 2.1 |
| Ram I | 1.3 | 67.7 | 47.0 | 7.3 | 3.0 | 3.2 |
| Touchdown | 1.1 | 73.1 | 75.0 | 7.6 | 2.1 | 2.3 |
| Victa | 1.7 | 74.9 | 58.3 | 10.0 | 4.7 | 3.5 |
| LSD (.05) | 0.68 | 7.35 | 8.62 | 0.66 | 0.72 | 0.50 |

*Panicle Nodding Rating Scale: 1–9; 9 = most nodding

TABLE 4

Morphological Comparison of Spikelets of Ba 73-381 and Other Kentucky Bluegrass Varieties in the Greenhouse at Marysville, Ohio

| | Spikelet | | | | Number of Florets Per Spikelet | |
|---|---|---|---|---|---|---|
| | Lower Whorl | | Third Whorl | | | |
| Variety | Length (mm) | Width (mm) | Length (mm) | Width (mm) | Lower Whorl | Third Whorl |
| Ba 73-381 | 4.7 | 2.4 | 4.6 | 2.6 | 2.7 | 2.7 |
| Ba 73-366 | 4.6 | 2.5 | 4.7 | 2.6 | 2.6 | 2.8 |
| Abbey | 4.4 | 2.2 | 4.5 | 2.2 | 3.0 | 3.0 |
| Adelphi | 4.6 | 2.2 | 4.8 | 2.2 | 4.4 | 4.4 |
| America | 4.6 | 2.2 | 4.4 | 2.3 | 4.5 | 4.3 |
| Baron | 5.4 | 2.8 | 5.4 | 3.1 | 4.0 | 4.2 |
| Bristol | 4.9 | 2.4 | 5.0 | 2.5 | 4.2 | 4.5 |
| Chateau | 4.4 | 2.4 | 4.4 | 2.4 | 3.4 | 3.5 |
| Coventry | 4.4 | 2.2 | 4.5 | 2.4 | 3.2 | 3.5 |
| Eclipse | 4.6 | 2.4 | 4.6 | 2.4 | 3.6 | 3.6 |
| Georgetown | 5.0 | 2.3 | 5.0 | 2.6 | 4.8 | 4.9 |
| Gnome | 4.6 | 2.5 | 4.6 | 2.9 | 3.2 | 3.2 |
| Kelly | 5.1 | 2.5 | 5.2 | 2.8 | 3.7 | 3.8 |
| Marquis | 4.3 | 2.2 | 4.4 | 2.3 | 3.1 | 2.9 |
| Midnight | 5.3 | 2.5 | 5.5 | 2.4 | 4.4 | 4.7 |
| Nassau | 4.7 | 2.6 | 4.8 | 3.0 | 4.2 | 4.3 |
| Ram I | 5.4 | 2.6 | 5.3 | 2.8 | 3.6 | 3.4 |
| Touchdown | 5.1 | 2.9 | 4.8 | 2.8 | 4.1 | 4.0 |
| Victa | 4.5 | 2.5 | 4.5 | 2.4 | 3.3 | 3.2 |
| LSD (.05) | 0.41 | 0.35 | 0.38 | 0.35 | 0.58 | 0.53 |

TABLE 5

Morphological Comparison of Glumes of Ba 73-381 and Other Kentucky Bluegrass Varieties in the Greenhouse at Marysville, Ohio

| | Glume Length (mm) | | | |
|---|---|---|---|---|
| | Outer | | Inner | |
| Variety | Lowest Whorl | Third Whorl | Lowest Whorl | Third Whorl |
| Ba 73-381 | 2.8 | 2.9 | 3.2 | 3.1 |
| Ba 73-366 | 2.8 | 2.8 | 3.2 | 3.1 |
| Abbey | 2.7 | 2.7 | 3.1 | 3.1 |
| Adelphi | 2.7 | 2.6 | 3.0 | 3.1 |
| America | 2.1 | 2.1 | 2.5 | 2.5 |
| Baron | 3.1 | 3.2 | 3.6 | 3.7 |
| Bristol | 2.8 | 3.0 | 3.3 | 3.4 |

TABLE 5-continued

Morphological Comparison of Glumes of Ba 73-381 and Other Kentucky Bluegrass Varieties in the Greenhouse at Marysville, Ohio

| | | | | |
|---|---|---|---|---|
| Chateau | 2.8 | 2.9 | 3.1 | 3.2 |
| Coventry | 2.7 | 2.8 | 3.1 | 3.1 |
| Eclipse | 3.0 | 3.0 | 3.4 | 3.4 |
| Georgetown | 2.8 | 2.8 | 3.1 | 3.1 |
| Gnome | 2.8 | 2.9 | 3.3 | 3.3 |
| Kelly | 3.0 | 3.1 | 3.4 | 3.5 |
| Marquis | 2.8 | 2.7 | 3.1 | 3.1 |
| Midnight | 2.6 | 2.6 | 3.0 | 3.1 |
| Nassau | 2.6 | 2.7 | 2.9 | 3.0 |
| Ram I | 2.9 | 3.0 | 3.6 | 3.5 |
| Touchdown | 3.3 | 3.3 | 3.8 | 3.8 |
| Victa | 2.8 | 2.7 | 3.1 | 3.1 |
| LSD (.05) | 0.23 | 0.22 | 0.22 | 0.23 |

| | Glume Hairs | | | |
|---|---|---|---|---|
| Variety | Lowest Outer | Whorl Inner | Third Outer | Whorl Inner |
| Ba 73-381 | 1.7 | 2.3 | 2.1 | 2.3 |
| Ba 73-366 | 1.7 | 1.3 | 1.3 | 2.0 |
| Abbey | 0.6 | 0.9 | 1.0 | 1.0 |
| Adelphi | 0.6 | 2.7 | 1.1 | 1.9 |
| America | 0.2 | 0.5 | 0.3 | 0.3 |
| Baron | 4.8 | 4.4 | 4.2 | 4.6 |
| Bristol | 1.0 | 2.2 | 0.8 | 2.2 |
| Chateau | 1.5 | 2.6 | 2.0 | 1.8 |
| Coventry | 1.5 | 2.7 | 1.6 | 2.4 |
| Eclipse | 1.5 | 1.9 | 1.8 | 1.9 |
| Georgetown | 1.7 | 2.7 | 1.2 | 2.5 |
| Gnome | 1.0 | 1.9 | 1.2 | 1.6 |
| Kelly | 1.3 | 1.5 | 1.1 | 0.8 |
| Marquis | 0.9 | 1.1 | 1.7 | 1.8 |
| Midnight | 1.8 | 2.8 | 1.0 | 2.4 |
| Nassau | 2.1 | 2.6 | 4.2 | 4.4 |
| Ram I | 1.1 | 2.3 | 0.7 | 1.2 |
| Touchdown | 0.7 | 2.1 | 1.1 | 1.4 |
| Victa | 0.8 | 1.1 | 1.1 | 1.3 |
| LSD (.05) | 0.9 | 0.9 | 0.9 | 0.9 |

TABLE 6

Morphological Comparison of Flag Leaves of Ba 73-381 and Other Kentucky Bluegrass Varieties in the Greenhouse at Marysville, Ohio

| Sheath[4] Variety | Length (cm) | Width (mm) | Thickness (mm) | Leaf Angle[1] | Leaf Curve[2] |
|---|---|---|---|---|---|
| Ba 73-381 | 4.3 | 3.5 | 0.223 | 1.9 | 5.0 |
| Ba 73-366 | 4.5 | 3.6 | 0.180 | 5.1 | 4.4 |
| Abbey | 3.8 | 3.4 | 0.145 | 2.7 | 4.1 |
| Adelphi | 5.7 | 3.4 | 0.178 | 5.2 | 5.0 |
| America | 4.3 | 2.6 | 0.211 | 4.6 | 5.0 |
| Baron | 7.0 | 4.2 | 0.152 | 9.2 | 4.4 |
| Bristol | 4.3 | 3.2 | 0.211 | 2.3 | 5.0 |
| Chateau | 4.0 | 2.7 | 0.193 | 3.4 | 2.0 |
| Coventry | 3.7 | 3.0 | 0.140 | 0.7 | 4.3 |
| Eclipse | 3.9 | 3.2 | 0.193 | 8.7 | 5.0 |
| Georgetown | 5.7 | 2.8 | 0.221 | 1.9 | 5.0 |
| Gnome | 4.5 | 3.5 | 0.185 | 4.3 | 5.0 |
| Kelly | 4.8 | 4.1 | 0.178 | 3.1 | 4.4 |
| Marquis | 5.5 | 3.6 | 0.241 | 2.7 | 4.6 |
| Midnight | 3.8 | 2.6 | 0.189 | 1.1 | 5.0 |
| Nassau | 6.0 | 3.7 | 0.191 | 5.9 | 4.7 |
| Ram I | 3.4 | 3.1 | 0.191 | 1.0 | 4.8 |
| Touchdown | 4.1 | 2.7 | 0.163 | 3.4 | 4.1 |
| Victa | 3.9 | 3.7 | 0.267 | 2.1 | 4.6 |
| LSD (.05) | 1.0 | 0.4 | 0.02 | 2.5 | 0.4 |

| Sheath[4] Variety | Ligule (mm) | Hairs[3] on Leaf Margin | Ligule | Color |
|---|---|---|---|---|
| Ba 73-381 | 1.3 | 0.4 | 3.6 | 1.5 |
| Ba 73-366 | 1.5 | 0.4 | 2.2 | 0.5 |
| Abbey | 1.3 | 0.8 | 1.6 | 0.2 |
| Adelphi | 1.1 | 1.8 | 1.6 | 0.4 |
| America | 0.6 | 0.4 | 0.7 | 1.9 |
| Baron | 1.2 | 1.0 | 3.8 | 2.6 |
| Bristol | 0.6 | 0.4 | 1.9 | 2.0 |

TABLE 6-continued

Morphological Comparison of Flag Leaves of Ba 73-381 and Other Kentucky Bluegrass Varieties in the Greenhouse at Marysville, Ohio

| | | | | |
|---|---|---|---|---|
| Chateau | 0.9 | 1.1 | 3.1 | 0.3 |
| Coventry | 0.9 | 0.8 | 1.7 | 2.0 |
| Eclipse | 1.1 | 1.0 | 1.0 | 0.2 |
| Georgetown | 0.6 | 0.6 | 2.0 | 2.0 |
| Gnome | 0.8 | 0.9 | 3.2 | 1.5 |
| Kelly | 1.5 | 1.1 | 2.5 | 2.2 |
| Marquis | 0.8 | 0.5 | 3.8 | 1.5 |
| Midnight | 0.4 | 0.4 | 0.3 | 2.0 |
| Nassau | 1.1 | 2.6 | 2.4 | 0.8 |
| Ram I | 0.7 | 0.5 | 1.3 | 2.0 |
| Touchdown | 1.1 | 1.0 | 1.0 | 7.7 |
| Victa | 1.3 | 1.0 | 0.8 | 0.5 |
| LSD (.05) | 0.17 | 0.47 | 0.7 | 0.76 |

[1]Degrees from the stem
[2]Rating Scale: 1–9; 1 = curves up; 5 = no curve; 9 = curves down
[3]Rating Scale: 0–9; 0 = none; 9 = many
[4]Rating Scale: 0–9; 0 = no color; 9 = dark purple

TABLE 7

Morphological Comparison of Peduncles, Culms, Node Numbers Per Culm and Internode Length of Ba 73-381 and Other Kentucky Bluegrass Varieties in the Greenhouse at Marysville, OH

| Variety (cm) | Peduncle Length (cm) | Peduncle Width (mm) | Culm Length (cm) | Nodes Per Culm | Top Internode Length |
|---|---|---|---|---|---|
| Ba 73-381 | 24.3 | 0.808 | 39.5 | 3.1 | 10.8 |
| Ba 73-366 | 26.4 | 0.704 | 42.7 | 4.1 | 9.2 |
| Abbey | 23.2 | 0.655 | 41.3 | 4.1 | 11.0 |
| Adelphi | 24.5 | 0.665 | 40.0 | 4.0 | 10.4 |
| America | 16.2 | 0.622 | 31.8 | 3.1 | 11.0 |
| Baron | 34.0 | 0.701 | 52.8 | 4.2 | 12.8 |
| Bristol | 22.9 | 0.734 | 43.5 | 4.0 | 12.6 |
| Chateau | 20.7 | 0.607 | 38.9 | 4.4 | 9.9 |
| Coventry | 19.6 | 0.487 | 34.7 | 4.5 | 7.9 |
| Eclipse | 23.7 | 0.658 | 39.2 | 4.9 | 9.9 |
| Georgetown | 21.7 | 0.683 | 37.5 | 3.2 | 11.1 |
| Gnome | 19.4 | 0.836 | 35.3 | 3.1 | 9.2 |
| Kelly | 29.4 | 0.752 | 46.6 | 3.6 | 11.8 |
| Marquis | 27.1 | 0.831 | 34.1 | 3.4 | 7.8 |
| Midnight | 20.5 | 0.722 | 29.5 | 2.8 | 7.6 |
| Nassau | 25.0 | 0.663 | 36.0 | 3.9 | 7.4 |
| Ram I | 22.2 | 0.694 | 30.5 | 2.5 | 6.6 |
| Touchdown | 23.6 | 0.519 | 38.0 | 4.0 | 8.4 |
| Victa | 21.2 | 0.808 | 37.9 | 3.7 | 10.3 |
| LSD (.05) | 3.2 | 0.08 | 3.3 | 0.4 | 1.9 |

TABLE 8

Morphological Comparison of Vegetative Leaves of Ba 73-381 and Other Kentucky Bluegrass Varieties in the Greenhouse at Marysville, OH

| Variety | Length (cm) | Width (mm) | Thickness (mm) | Leaf Angle[1] | Curve[2] |
|---|---|---|---|---|---|
| Ba 73-381 | 22.1 | 3.3 | 0.300 | 62.5 | 8.2 |
| Ba 73-366 | 22.9 | 3.8 | 0.401 | 53.0 | 7.1 |
| Abbey | 20.7 | 3.6 | 0.277 | 51.3 | 7.4 |
| Adelphi | 19.4 | 3.7 | 0.279 | 67.0 | 4.6 |
| America | 21.4 | 3.1 | 0.325 | 66.0 | 6.4 |
| Baron | 18.2 | 4.3 | 0.290 | 35.0 | 4.4 |
| Bristol | 18.2 | 3.7 | 0.320 | 65.5 | 6.9 |
| Chateau | 23.1 | 3.3 | 0.328 | 39.7 | 5.4 |
| Coventry | 23.4 | 3.6 | 0.249 | 63.0 | 7.3 |
| Eclipse | 20.3 | 4.4 | 0.302 | 65.5 | 5.4 |
| Georgetown | 19.5 | 3.6 | 0.287 | 56.7 | 5.8 |
| Gnome | 18.2 | 2.9 | 0.290 | 43.2 | 6.6 |
| Kelly | 22.8 | 3.9 | 0.300 | 55.5 | 7.0 |
| Marquis | 19.7 | 3.7 | 0.376 | 46.8 | 7.8 |
| Midnight | 19.5 | 3.5 | 0.310 | 63.3 | 5.0 |
| Nassau | 16.3 | 3.7 | 0.292 | 63.2 | 4.9 |
| Ram I | 19.1 | 3.6 | 0.271 | 70.8 | 6.5 |
| Touchdown | 16.7 | 3.7 | 0.243 | 51.3 | 4.0 |
| Victa | 21.5 | 3.6 | 0.360 | 56.3 | 6.7 |
| LSD (.05) | 3.5 | 0.43 | 0.04 | 15.9 | 1.5 |

TABLE 8-continued

Morphological Comparison of Vegetative Leaves of Ba 73-381 and Other Kentucky Bluegrass Varieties in the Greenhouse at Marysville, OH

| Variety | Ligule (mm) | Hairs[3] Ligule | Hairs[3] Leaf Margin | Leaf Roughness[4] | Sheath Color[5] |
|---|---|---|---|---|---|
| Ba 73-381 | 0.16 | 3.2 | 0.7 | 8.2 | 2.0 |
| Ba 73-366 | 0.23 | 5.2 | 4.2 | 8.5 | 0.0 |
| Abbey | 0.32 | 4.4 | 2.8 | 7.7 | 0.0 |
| Adelphi | 0.34 | 2.6 | 3.4 | 8.8 | 0.0 |
| America | 0.12 | 1.7 | 2.1 | 8.4 | 2.0 |
| Baron | 0.33 | 4.6 | 3.6 | 7.4 | 0.4 |
| Bristol | 0.12 | 2.6 | 3.0 | 8.9 | 2.0 |
| Chateau | 0.22 | 3.3 | 3.1 | 7.8 | 0.5 |
| Coventry | 0.32 | 3.1 | 2.4 | 8.1 | 0.3 |
| Eclipse | 0.38 | 2.8 | 2.6 | 9.0 | 0.2 |
| Georgetown | 0.14 | 2.5 | 2.4 | 8.5 | 2.0 |
| Gnome | 0.23 | 1.6 | 0.8 | 7.5 | 1.4 |
| Kelly | 0.34 | 4.6 | 2.4 | 8.8 | 0.0 |
| Marquis | 0.21 | 3.6 | 1.1 | 6.8 | 1.1 |
| Midnight | 0.10 | 1.3 | 1.6 | 7.7 | 2.0 |
| Nassau | 0.34 | 2.5 | 3.3 | 8.5 | 1.4 |
| Ram I | 0.09 | 1.8 | 2.0 | 7.7 | 2.0 |
| Touchdown | 0.29 | 1.4 | 1.3 | 7.9 | 8.0 |
| Victa | 0.26 | 2.3 | 1.7 | 7.9 | 0.1 |
| LSD (.05) | 0.04 | 0.79 | 0.70 | 0.89 | 0.57 |

[1]Degrees from stem
[2]Rating Scale: 1–9; 1 = curve up; 5 = no curve; 9 = curve down
[3]Rating Scale: 0–9; 0 = none; 9 = many
[4]Rating Scale: 1–9; 1 = rough; 9 = smooth
[5]Rating Scale: 0–9; 0 = no color; 9 = dark purple Ba 73-381 has performed well throughout the U.S.A. as exhibited by medium to high turf quality ratings in a number of locations across the U.S.A. in comparison to other Kentucky bluegrass varieties. In addition, it has a pleasant medium green color which can be maintained throughout the growing season, a substantial level of living ground cover and a medium wide leaf.

Comparisons of Ba 73-381 with other Kentucky bluegrass varieties for quality are set forth hereinafter in Tables 9–12:

TABLE 9

Comparison of Turfgrass Quality of Ba 73-381 and Other Kentucky bluegrass Varieties at Various Locations in the U.S.A.

| Variety | Locations[1] A | B | C | D | E | F | G |
|---|---|---|---|---|---|---|---|
| Ba 73-381 | 8.0 | 6.9 | 5.4 | 6.5 | 5.3 | 6.8 | 5.1 |
| Ba 73-366 | 7.7 | 7.2 | 5.3 | 6.5 | 5.0 | 6.6 | 4.9 |
| Abbey | 7.0 | 6.9 | 5.5 | 5.4 | 4.9 | 6.8 | 5.0 |
| Able I | 7.7 | 7.5 | 5.9 | 7.0 | 5.7 | 6.5 | 5.0 |
| A-34 | 8.7 | 6.8 | 4.6 | 7.0 | 5.4 | 6.2 | 4.9 |
| Banff | 8.7 | 6.6 | 6.1 | 6.8 | 4.6 | 6.7 | 5.1 |
| Baron | 7.7 | 7.2 | 5.7 | 7.0 | 5.7 | 7.0 | 5.7 |
| Classic | 8.3 | 6.9 | 6.2 | 6.8 | 4.3 | 6.7 | 4.8 |
| Coventry | 8.7 | 6.3 | 5.9 | 6.7 | 5.8 | 7.0 | 4.7 |
| Eclipse | 8.3 | 6.7 | 6.5 | 6.2 | 5.1 | 7.3 | 5.0 |
| Estate | 8.7 | 7.0 | 5.5 | 7.0 | 6.0 | 6.4 | 5.0 |
| Georgetown | 8.0 | 6.6 | 6.6 | 6.5 | 4.9 | 6.9 | 4.4 |
| Glade | 9.0 | 7.4 | 7.5 | 7.0 | 5.6 | 7.6 | 4.3 |
| Gnome | 8.0 | 6.8 | 5.0 | 7.0 | 5.0 | 7.0 | 3.9 |
| Haga | 8.0 | 6.7 | 6.3 | 7.0 | 5.1 | 6.8 | 4.5 |
| Kelly | 7.7 | 7.2 | 5.8 | 6.5 | 5.0 | 6.8 | 5.0 |
| Kenblue | 7.7 | 6.4 | 3.3 | 7.0 | 3.8 | 6.2 | 3.9 |
| Marquis | 8.0 | 6.8 | 5.3 | 6.7 | 5.5 | 6.5 | 4.9 |
| Merion | 6.7 | 5.1 | 2.7 | 5.2 | 4.2 | 4.8 | 3.2 |
| Merit | 8.0 | 6.9 | 4.9 | 6.5 | 4.1 | 6.6 | 5.0 |
| Midnight | 8.0 | 7.1 | 8.3 | 6.7 | 4.7 | 7.7 | 4.9 |
| Monopoly | 7.7 | 6.5 | 5.0 | 7.3 | 4.8 | 6.1 | 5.1 |
| Nassau | 8.0 | 6.9 | 6.4 | 6.0 | 5.5 | 6.3 | 4.8 |
| Ram I | 8.0 | 7.8 | 6.0 | 7.3 | 5.2 | 7.0 | 5.3 |
| South Dakota | 7.0 | 6.6 | 3.0 | 6.2 | 2.1 | 4.9 | 3.0 |
| Touchdown | 9.0 | 7.2 | 4.2 | 6.7 | 3.3 | 6.5 | 4.7 |

TABLE 9-continued

Comparison of Turfgrass Quality of Ba 73-381 and Other Kentucky bluegrass Varieties at Various Locations in the U.S.A.

| Variety | Locations[1] A | B | C | D | E | F | G |
|---|---|---|---|---|---|---|---|
| LSD (.05) | 1.2 | 0.8 | 0.9 | 1.1 | 1.1 | 0.5 | 0.9 |

Rating Scale 1–9; 9 = ideal turf
[1]Locations:
A. Fort Collins, CO;
B. Ames, IA;
C. Adelphia, N.J.;
D. Marysville, OH;
E. Hubbard, OR;
F. Beltsville, MD;
G. Blacksburg, Va.

TABLE 10

A Comparison of Quality of Ba 73-381 and other Kentucky Bluegrass Varieties at Prince Fredrick, Maryland Determined at Various Time Periods A–E

| Variety | Quality[1] A | B | Mean of A and B | C | D | E | Mean of C–E |
|---|---|---|---|---|---|---|---|
| Ba 73-381 | 2.2 | 2.4 | 2.3 | 2.9 | 2.6 | 3.1 | 2.8 |
| Adelphi | 2.0 | 1.9 | 1.9 | 2.7 | 2.6 | 3.1 | 2.8 |
| Bristol | 1.9 | 1.8 | 1.9 | 2.6 | 2.6 | 3.0 | 2.8 |
| Glade | 1.9 | 1.7 | 1.8 | 2.5 | 1.4 | 2.5 | 2.1 |
| Kelly | 2.0 | 1.9 | 1.9 | 2.8 | 2.5 | 3.0 | 2.8 |
| Merion | 2.0 | 2.1 | 2.0 | 2.1 | 1.6 | 2.5 | 2.1 |
| Merit | 2.7 | 1.9 | 2.0 | 1.6 | 1.4 | 2.1 | 1.7 |
| Nugget | 1.8 | 1.8 | 1.8 | 1.0 | 1.0 | 1.0 | 1.0 |
| Park | 2.1 | 2.2 | 2.2 | 1.5 | 1.4 | 2.3 | 1.7 |
| Vantage | 2.1 | 2.2 | 2.2 | 2.8 | 2.7 | 3.0 | 2.8 |
| Victa | 1.7 | 1.8 | 1.8 | 2.9 | 2.8 | 3.1 | 2.9 |
| Mean | 1.9 | 1.9 | 1.9 | 2.5 | 2.3 | 2.8 | 2.5 |
| LSD (.05) | 1.3 | 1.3 | 0.72 | 1.0 | 0.62 | | |

[1]Rating Scale: 1–5; 5 = best

TABLE 11

A Comparison of Quality of Ba 73-381 and Other Kentucky Bluegrass Varieties at Marysville, OH Determined at Times A and B

| Variety | Quality A | B |
|---|---|---|
| Ba 73-381 | 6.0 | 7.3 |
| Ba 73-366 | 7.0 | 7.3 |
| Abbey | 6.3 | 7.0 |
| Amazon | 5.3 | 5.3 |
| Baron | 6.0 | 6.3 |
| Bristol | 5.0 | 6.0 |
| Coventry | 6.0 | 6.7 |
| Cynthia | 5.7 | 6.7 |
| Gnome | 6.0 | 6.7 |
| Haga | 6.7 | 7.0 |
| Kenblue | 6.3 | 6.3 |
| Merion | 5.0 | 6.3 |
| Merit | 6.3 | 6.7 |
| Midnight | 6.0 | 6.0 |
| Monopoly | 6.7 | 7.7 |
| Park | 6.3 | 6.0 |
| Ram I | 6.3 | 7.7 |
| South Dakota | 4.7 | 6.0 |
| Victa | 6.0 | 7.3 |
| Mean | 5.9 | 6.5 |
| LSD (.05) | 1.0 | 1.0 |

Rating Scale: 1–9; 9 = ideal turf

TABLE 12

A Comparison of Quality of Ba 73-381 and Other Kentucky Bluegrass Varieties Grown Under Shade Conditions at Marysville, OH at Various Time Periods A–F

| Variety | Quality A | B | C | D | E | F |
|---|---|---|---|---|---|---|
| Ba 73-381 | 2.5 | 2.0 | 2.4 | 2.1 | 2.4 | 2.6 |

TABLE 12-continued

A Comparison of Quality of Ba 73-381 and Other Kentucky Bluegrass Varieties Grown Under Shade Conditions at Marysville, OH at Various Time Periods A–F

| Variety | Quality A | B | C | D | E | F |
|---|---|---|---|---|---|---|
| Ba 73-366 | 2.1 | 2.0 | 2.2 | 2.1 | 2.2 | 2.5 |
| Adelphi | 2.1 | 2.0 | 2.2 | 2.1 | 2.2 | 2.3 |
| Bristol | 2.0 | 2.1 | 2.2 | 2.2 | 1.9 | 2.3 |
| Merion | 2.2 | 1.9 | 2.2 | 2.0 | 2.3 | 2.5 |
| Newport | 2.0 | 2.0 | 2.0 | 1.8 | 2.1 | 2.1 |
| Nugget | 1.8 | 1.8 | 1.9 | 1.9 | 2.0 | 2.1 |
| Park | 1.7 | 1.8 | 1.9 | 1.9 | 2.0 | 2.1 |
| Vantage | 1.7 | 1.9 | 2.1 | 2.1 | 2.1 | 2.3 |
| Victa | 2.2 | 2.0 | 2.3 | 2.1 | 2.1 | 2.5 |
| Mean | 1.9 | 2.0 | 2.0 | 2.0 | 2.0 | 2.2 |
| LSD (.05) | 0.3 | 0.13 | 0.14 | 0.19 | 0.19 | 0.2 |

Rating Scale: 1–5; 5 = best

With regard to a comparative analysis conducted for purposes of determining color of Ba 73-381 plants relative to other Kentucky bluegrass varieties, readings were taken of the the vegetative color of Ba 73-381 during mid-May while the turf was actively growing with adequate nutrient and water availability. The readings were taken in full sun with several actively growing leaves being compared, one at a time, utilizing color chips from the Munsell Book of Color as a reference. On this basis, the color of Ba 73-381 was determined to be 5 GY 4/4. During the same time period, the color of similar leaves of other Kentucky bluegrass varieties were determined by the same procedure to be as follows: Ba 73-366 -5 GY 4/4; Ba 73-540 - 5 GY 4/4; Abbey - 5 GY $\frac{3}{4}$; and Coventry - 5 GY 4/4. However, it should be noted that the general apparent color of turf does not always correlate directly with the color of the individual actively growing leaves within the turf and that turf color varies with nutrient level and time of year with some varieties being darker or lighter green depending on such factors.

Further comparisons of Ba 73-381 with other Kentucky bluegrass varieties for genetic color are set forth hereinafter in Table 13:

TABLE 13

A Comparison of Genetic Color of Ba 73-381 and Other Kentucky Bluegrass Varieties at Various Locations in the U.S.A.

| Variety | Locations[1] A | B | C | D | E | E | F | Mean |
|---|---|---|---|---|---|---|---|---|
| Ba 73-381 | 5.0 | 6.7 | 5.0 | 5.4 | 7.7 | 6.7 | 5.7 | 6.0 |
| Ba 73-366 | 4.7 | 5.7 | 4.3 | 4.3 | 7.0 | 7.0 | 5.7 | 5.5 |
| Abbey | 4.0 | 6.2 | 5.3 | 4.3 | 7.0 | 6.0 | 6.7 | 5.6 |
| Able I | 4.7 | 7.3 | 8.0 | 6.0 | 7.3 | 7.0 | 6.0 | 6.6 |
| A-34 | 4.0 | 5.0 | 3.7 | 4.3 | 7.0 | 6.0 | 5.3 | 5.0 |
| Banff | 5.7 | 4.7 | 4.0 | 5.0 | 6.7 | 6.0 | 4.0 | 5.1 |
| Baron | 4.0 | 6.0 | 6.0 | 5.0 | 7.3 | 7.3 | 6.3 | 6.0 |
| Classic | 5.3 | 5.2 | 4.3 | 5.0 | 6.7 | 5.7 | 4.3 | 5.2 |
| Coventry | 5.3 | 5.8 | 5.7 | 4.3 | 7.0 | 6.7 | 6.3 | 5.9 |
| Eclipse | 5.0 | 7.0 | 6.3 | 5.3 | 7.3 | 6.3 | 7.0 | 6.3 |
| Estate | 4.7 | 6.2 | 5.7 | 5.3 | 6.7 | 6.7 | 5.7 | 5.8 |
| Georgetown | 4.0 | 5.0 | 4.7 | 5.0 | 7.0 | 6.0 | 5.0 | 5.2 |
| Glade | 5.3 | 7.3 | 7.0 | 6.0 | 7.0 | 7.0 | 7.3 | 6.7 |
| Gnome | 5.3 | 5.5 | 5.7 | 4.7 | 7.3 | 7.0 | 6.7 | 6.0 |
| Haga | 4.3 | 5.0 | 4.0 | 5.0 | 7.0 | 6.0 | 4.3 | 5.1 |
| Kelly | 4.7 | 6.2 | 4.7 | 4.0 | 7.0 | 6.3 | 6.3 | 5.6 |
| Kenblue | 3.7 | 4.3 | 3.7 | 3.7 | 7.0 | 6.0 | 4.0 | 4.6 |
| Marquis | 5.0 | 6.5 | 5.3 | 5.0 | 7.3 | 7.0 | 6.7 | 6.1 |
| Merion | 4.3 | 6.7 | 6.3 | 4.3 | 7.0 | 5.3 | 6.0 | 5.7 |
| Merit | 5.0 | 6.3 | 4.7 | 4.3 | 7.0 | 7.0 | 5.3 | 5.7 |
| Midnight | 6.0 | 7.7 | 8.3 | 6.3 | 8.0 | 7.7 | 6.0 | 7.1 |
| Monopoly | 4.7 | 4.2 | 4.0 | 4.0 | 6.0 | 6.7 | 4.0 | 4.8 |
| Nassau | 5.7 | 6.7 | 5.7 | 5.0 | 8.0 | 6.7 | 4.7 | 6.0 |
| Ram I | 6.0 | 7.0 | 7.0 | 6.0 | 7.3 | 7.0 | 6.7 | 6.7 |
| South Dakota | 4.0 | 5.2 | 3.0 | 3.0 | 7.0 | 5.3 | 4.0 | 4.5 |

TABLE 13-continued

A Comparison of Genetic Color of Ba 73-381 and Other Kentucky Bluegrass Varieties at Various Locations in the U.S.A.

| Variety | Locations[1] A | B | C | D | E | E | F | Mean |
|---|---|---|---|---|---|---|---|---|
| Touchdown | 4.7 | 6.3 | 4.3 | 4.7 | 7.3 | 6.3 | 5.0 | 5.5 |
| LSD (.05) | 1.3 | 1.3 | 0.9 | 0.7 | 0.7 | 0.7 | 1.4 | 0.5 |

Ratings Scale: 1–9; 9 = dark green
[1]Locations:
A. Fort Collins, CO;
B. Post Falls, ID;
C. North Brunswick, NJ;
D. Marysville, OH;
E. Pooled data from Halsey, Hubbard and Gervais, OR;
F. Haymarket, VA Ba 73-381 developes good density and a high degree of living ground cover. It has a moderately wide blade as identified by leaf texture data. Also, Ba 73-381 has good seedling vigor. Data for these performance characteristics are presented in Tables 14–17 as follows:

TABLE 14

Comparison of Density of Ba 73-381 and Other Kentucky Bluegrass Varieties at Marysville, OH

| Variety | Density |
|---|---|
| Ba 73-381 | 6.6 |
| Ba 73-366 | 6.3 |
| Abbey | 6.0 |
| Aspen | 5.7 |
| A-34 | 6.0 |
| Banff | 6.3 |
| Baron | 6.3 |
| Bristol | 5.3 |
| Classic | 6.7 |
| Coventry | 6.7 |
| Eclipse | 6.3 |
| Estate | 7.3 |
| Georgetown | 6.3 |
| Glade | 6.7 |
| Gnome | 6.3 |
| Haga | 6.3 |
| Kelly | 6.0 |
| Kenblue | 6.0 |
| Marquis | 6.3 |
| Merion | 4.7 |
| Merit | 6.7 |
| Midnight | 6.3 |
| Monopoly | 6.7 |
| Nassau | 5.7 |
| Ram I | 7.0 |
| Touchdown | 6.0 |
| Victa | 6.7 |
| Mean | 6.1 |
| LSD (.05) | 1.2 |

Rating Scale: 1–9; 9 = most dense cover

TABLE 15

Comparison of Percent Living Ground Cover in the Fall of Ba 73-381, and other Kentucky Bluegrass Varieties at Haymarket, VA

| Variety | % Living Ground Cover |
|---|---|
| Ba 73-381 | 50.0 |
| Ba 73-366 | 21.7 |
| Abbey | 31.7 |
| Able I | 36.7 |
| A-34 | 46.7 |
| Banff | 46.7 |
| Baron | 30.0 |
| Classic | 40.0 |
| Coventry | 43.3 |
| Eclipse | 33.3 |
| Estate | 38.3 |
| Georgetown | 55.0 |
| Glade | 43.3 |
| Gnome | 38.3 |

TABLE 15-continued

Comparison of Percent Living Ground Cover in the Fall of Ba 73-381, and other Kentucky Bluegrass Varieties at Haymarket, VA

| Variety | % Living Ground Cover |
|---|---|
| Haga | 58.3 |
| Kelly | 43.3 |
| Kenblue | 11.7 |
| marquis | 35.0 |
| Merion | 40.0 |
| Merit | 28.3 |
| Midnight | 11.7 |
| Monopoly | 43.3 |
| Nassau | 43.3 |
| Ram I | 28.3 |
| South Dakota | 30.0 |
| Touchdown | 26.7 |
| LSD (.05) | 27.4 |

TABLE 16

Comparison of Leaf Texture of Ba 73-381 and Other Kentucky Bluegrass Varieties at Martinsville, NJ

| Variety | Leaf Texture |
|---|---|
| Ba 73-381 | 4.0 |
| Ba 73-366 | 4.3 |
| Abbey | 5.0 |
| Able I | 5.7 |
| A-34 | 4.3 |
| Banff | 5.3 |
| Baron | 5.0 |
| Classic | 5.3 |
| Coventry | 5.0 |
| Eclipse | 5.7 |
| Estate | 4.3 |
| Georgetown | 6.0 |
| Glade | 5.0 |
| Gnome | 5.3 |
| Haga | 5.7 |
| Kelly | 4.3 |
| Kenblue | 6.0 |
| Marquis | 4.3 |
| Merion | 4.0 |
| Merit | 4.7 |
| Midnight | 6.7 |
| Monopoly | 5.0 |
| Nassau | 5.0 |
| Ram I | 5.0 |
| South Dakota | 3.7 |
| Touchdown | 5.3 |
| LSD (.05) | 0.9 |

Rating Scale: 1–9; 9 = very fine

TABLE 17

A Comparison of Seedling Vigor of Ba 73-381 and Other Kentucky Bluegrass Varieties at Various Locations[1] in the U.S.A. and Canada

| Variety | Seedling Vigor Mean |
|---|---|
| Ba 73-381 | 6.3 |
| Ba 73-366 | 6.3 |
| Abbey | 6.4 |
| Able I | 6.3 |
| A-34 | 6.0 |
| Banff | 7.7 |
| Baron | 6.7 |
| Classic | 7.1 |
| Coventry | 6.1 |
| Eclipse | 6.1 |
| Estate | 6.1 |
| Georgetown | 7.0 |
| Glade | 6.7 |
| Gnome | 6.3 |
| Haga | 7.1 |
| Kelly | 6.6 |
| Kenblue | 7.4 |
| Marquis | 6.3 |

TABLE 17-continued

A Comparison of Seedling Vigor of Ba 73-381 and Other Kentucky Bluegrass Varieties at Various Locations[1] in the U.S.A. and Canada

| Variety | Seedling Vigor Mean |
|---|---|
| Merion | 2.6 |
| Merit | 6.4 |
| Midnight | 5.4 |
| Monopoly | 7.1 |
| Nassau | 6.4 |
| Ram I | 6.5 |
| South Dakota | 6.7 |
| Touchdown | 5.8 |
| LSD (.05) | 0.7 |

Rating Scale: 1–9; 9 = Maximum vigor
[2]Locations: Fort Collins, CO; Post Falls, ID; North Brunswick, NJ; Adelphia, NJ; Richmond Hill, Ontario; pooled data Halsey, Hubbard and Gervais, OR.

Turf diseases are one of the major causes of inconsistent and poor turf performance among locations and years. Ba 73-381 has been found to have a medium to high level of resistance to leaf spot, melting out and crown rot caused by *Drechslera poae* (formerly called *Helminthosporium vagans*); a medium to high level of resistance to several rust diseases caused by Puccinia spp., and to stripe smut caused by *Utilago striiformis*.

Comparisons of disease incidence of Ba 73-381 as compared with other bluegrass varieties in regard to leaf spot, rusts, dollarspot, and stripe smut are set forth in Tables 18–23. Additional comparisons are presented in Table 24–26 identifying high speed yields relative to other bluegrasses.

TABLE 18

Ccomparison of Leaf Spot Incidence in Ba 73-381 and Other Kentucky Bluegrass Varieties Grown Under Shade Conditions at Marysville, OH

| Variety | % Leaf Spot |
|---|---|
| Ba 73-381 | 0.0 |
| Ba 73-366 | 0.0 |
| Adelphi | 5.0 |
| America | 40.0 |
| Banff | 2.5 |
| Bristol | 0.0 |
| Classic | 5.0 |
| Eclipse | 2.5 |
| Georgetown | 7.5 |
| Glade | 7.5 |
| Kenblue | 10.0 |
| Merion | 0.0 |
| Merit | 0.0 |
| Nassau | 0.0 |
| Newport | 0.0 |
| Park | 50.0 |
| Ram I | 40.0 |
| Sydsport | 27.5 |
| Vantage | 2.5 |
| Victa | 2.5 |
| Mean | 9.8 |
| LSD (.05) | 26.7 |

TABLE 19

Comparison of Leaf Spot Incidence in Ba 73-381 and Other Kentucky Bluegrass Varieties at Marysville, OH

| Variety | Leaf Spot |
|---|---|
| Ba 73-381 | 7.3 |
| Ba 73-366 | 6.7 |
| Adelphi | 6.3 |
| Banff | 6.5 |
| Baron | 7.0 |
| Bonnieblue | 7.0 |
| Bristol | 7.3 |
| Classic | 6.0 |
| Eclipse | 7.0 |

TABLE 19-continued

Comparison of Leaf Spot Incidence in Ba 73-381 and Other Kentucky Bluegrass Varieties at Marysville, OH

| Variety | Leaf Spot |
|---|---|
| Georgetown | 6.3 |
| Glade | 5.3 |
| Kelly | 7.0 |
| Kenblue | 7.0 |
| Merion | 6.7 |
| Merit | 7.0 |
| Nassau | 7.0 |
| Newport | 6.7 |
| Park | 6.3 |
| Ram I | 6.0 |
| Vantage | 6.7 |
| Victa | 7.0 |
| Mean | 6.8 |
| LSD (.05) | 1.1 |

Ratings Scale: 1-9; 9 = no disease.

TABLE 20

Comparison of Powdery Mildew Incidence in Ba 73-381 and Other Kentucky Bluegrass Varieties Grown Under Shade Conditions at Marysville, OH During Time Periods A and B

| | % Powdery Mildew | |
|---|---|---|
| Variety | A | B |
| Ba 73-381 | 75.0 | 55.0 |
| Ba 73-366 | 80.0 | 27.5 |
| Adelphi | 35.0 | 37.5 |
| Bristol | 30.0 | 17.5 |
| Glade | 35.0 | 45.0 |
| Merion | 75.0 | 67.5 |
| Monopoly | 7.5 | 15.0 |
| Nassau | 27.5 | 45.0 |
| Park | 50.0 | 35.0 |
| Ram I | 50.0 | 42.5 |
| Vantage | 37.5 | 10.0 |
| Victa | 87.5 | 50.0 |
| Mean | 48.0 | 35.6 |
| LSD (.05) | 43.0 | 22.0 |

TABLE 21

Comparison of Stem Rust and Leaf Rust Incidence in Ba 73-381 and Other Kentucky Bluegrass Varieties at Kingston, R.I.

| Variety | Stem Rust | Leaf Rust |
|---|---|---|
| Ba 73-381 | 7.3 | 6.3 |
| Ba 73-366 | 6.7 | 5.7 |
| Abbey | 7.0 | 6.3 |
| Able I | 3.3 | 7.0 |
| A-34 | 4.3 | 6.0 |
| Banff | 7.7 | 7.0 |
| Baron | 7.0 | 8.3 |
| Classic | 8.0 | 8.7 |
| Coventry | 6.7 | 7.0 |
| Eclipse | 4.0 | 5.7 |
| Estate | 6.3 | 6.3 |
| Georgetown | 8.7 | 7.7 |
| Glade | 7.7 | 7.0 |
| Gnome | 7.0 | 6.7 |
| Haga | 8.0 | 7.0 |
| Kelly | 8.0 | 5.0 |
| Kenblue | 5.7 | 6.7 |
| Marquis | 6.7 | 6.3 |
| Merion | 1.0 | 2.3 |
| Merit | 6.3 | 6.0 |
| Midnight | 8.0 | 6.0 |
| Monopoly | 6.3 | 5.3 |
| Nassau | 8.0 | 7.0 |
| Ram I | 8.0 | 6.7 |
| South Dakota | 4.3 | 6.7 |
| Touchdown | 2.3 | 3.7 |
| LSD (.05) | 1.4 | 2.4 |

Rating Scale: 1-9; 9 = no disease

TABLE 22

Comparison of Stripe Rust Incidence in Ba 73-381 and Other Kentucky Bluegrass Varieties developed from pooled data at Halsey, Hubbard and Gervais, OR

| Variety | Strive Rust |
|---|---|
| Ba 73-381 | 4.7 |
| Ba 73-366 | 5.0 |
| Abbey | 4.3 |
| Able I | 6.0 |
| A-34 | 5.0 |
| Banff | 6.0 |
| Baron | 6.0 |
| Classic | 6.3 |
| Coventry | 5.0 |
| Eclipse | 6.0 |
| Estate | 5.7 |
| Georgetown | 6.3 |
| Glade | 3.0 |
| Gnome | 4.7 |
| Haga | 6.3 |
| Kelly | 5.0 |
| Kenblue | 3.3 |
| Marquis | 5.3 |
| Merion | 3.7 |
| Merit | 5.0 |
| Midnight | 4.7 |
| Monopoly | 5.3 |
| Nassau | 5.3 |
| Ram I | 6.0 |
| South Dakota | 4.0 |
| Touchdown | 3.0 |
| LSD (.05) | 1.2 |

Rating Scale: 1-9; 9 = no disease

TABLE 23

Comparison of Stripe Smut Incidence in Ba 73-381 and Other Kentucky Bluegrass Varieties at Marysville, OH

| Variety | Strive Smut |
|---|---|
| Ba 73-381 | 7.0 |
| Ba 73-366 | 6.3 |
| Adelphi | 7.7 |
| America | 6.7 |
| Banff | 8.0 |
| Baron | 8.0 |
| Bonnieblue | 8.0 |
| Bristol | 7.7 |
| Classic | 8.0 |
| Eclipse | 7.3 |
| Georgetown | 7.7 |
| Glade | 7.7 |
| Kelly | 6.3 |
| Kenblue | 7.0 |
| Merion | 7.7 |
| Merit | 5.7 |
| Nassau | 7.7 |
| Newport | 7.3 |
| Park | 6.7 |
| Ram I | 7.3 |
| Vantage | 7.3 |
| Victa | 5.0 |
| Mean | 7.0 |
| LSD (.05) | 1.2 |

Rating Scale: 1-9; 9 = least disease

TABLE 24

Comparison of Seed Yields of Ba 73-381 and Other Kentucky Bluegrass Varieties at Gervais, Oregon During Consecutive Growing Years A-D

| | Lbs/Acre | | | |
|---|---|---|---|---|
| Variety | A | B | C | D |
| Ba 73-381 | 626 | 1196 | 740 | 1261 |
| Bristol | 347 | 808 | 627 | 684 |
| Julia | 296 | 1016 | — | — |
| Kelly | 672 | 1136 | 760 | 1265 |
| Mosa | 322 | 1060 | — | — |
| Newport | 435 | 1256 | — | — |
| Victa | 780 | 1394 | 855 | 1287 |

TABLE 24-continued

Comparison of Seed Yields of Ba 73-381 and Other Kentucky Bluegrass Varieties at Gervais, Oregon During Consecutive Growing Years A–D

| | Lbs/Acre | | | |
|---|---|---|---|---|
| Variety | A | B | C | D |
| LSD (.05) | 140 | 134 | 105 | — |

TABLE 25

Comparison of Seed Yields in Pounds Per Acre for Ba 73-381 and Other Kentucky Bluegrass Varieties Over a 3 year Period at Gervais, Oregon

| | Lbs/Acre | | |
|---|---|---|---|
| Variety | Year 1 | Year 2 | Year 3 |
| Ba 73-381 | 970 | 1306 | 558 |
| Ba 73-366 | 920 | 1258 | 521 |
| Abbey | 1124 | 1314 | 629 |
| Apart | 1244 | 851 | 812 |
| Coventry | 786 | 914 | 649 |
| Newport | 1165 | 1002 | 1177 |

TABLE 25-continued

Comparison of Seed Yields in Pounds Per Acre for Ba 73-381 and Other Kentucky Bluegrass Varieties Over a 3 year Period at Gervais, Oregon

| | Lbs/Acre | | |
|---|---|---|---|
| Variety | Year 1 | Year 2 | Year 3 |
| LSD (.05) | 209 | 176 | 158 |

TABLE 26

Comparison of Seed Yields in Pounds Per Acre for Ba 73-381 and Other Kentucky Bluegrass Varieties at La Grande, Oregon

| Variety | Lbs/Acre |
|---|---|
| Ba 73-381 | 1,551 |
| Ba 73-366 | 1,612 |
| Abbey | 1,549 |
| Coventry | 1,046 |
| LSD (.05) | 160 |

What is claimed is:

1. A variety of Kentucky bluegrass, substantially as shown and described, characterized by a medium to high level of resistance to several serious diseases, including leaf spot and melting out disease, several rust diseases, and stripe smut, a desirable green color throughout the growing season, forms a turf of good quality under a wide variety of environmental conditions, has a moderately wide blade and a high level of seed yielding capacity.

* * * * *